(12) United States Patent
Durand et al.

(10) Patent No.: US 9,037,248 B2
(45) Date of Patent: May 19, 2015

(54) METHOD TO TREAT PAIN THROUGH ELECTRICAL STIMULATION OF NERVES

(75) Inventors: Dominique M. Durand, Solon, OH (US); Brian Wodlinger, Pittsburgh, PA (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 13/814,456

(22) PCT Filed: Aug. 10, 2011

(86) PCT No.: PCT/US2011/047190
§ 371 (c)(1),
(2), (4) Date: Feb. 5, 2013

(87) PCT Pub. No.: WO2012/021583
PCT Pub. Date: Feb. 16, 2012

(65) Prior Publication Data
US 2013/0138193 A1    May 30, 2013

Related U.S. Application Data

(60) Provisional application No. 61/372,341, filed on Aug. 10, 2010.

(51) Int. Cl.
*A61N 1/05*    (2006.01)
*A61N 1/36*    (2006.01)

(52) U.S. Cl.
CPC .......... *A61N 1/0556* (2013.01); *A61N 1/36071* (2013.01); *A61N 1/36171* (2013.01)

(58) Field of Classification Search
USPC .................................................. 607/118, 46
See application file for complete search history.

(56) References Cited

U.S. PATENT DOCUMENTS

| | | |
|---|---|---|
| 5,400,784 A | 3/1995 | Durand et al. |
| 5,634,462 A | 6/1997 | Tyler et al. |
| 6,456,866 B1 | 9/2002 | Tyler et al. |
| 6,600,956 B2 | 7/2003 | Maschino et al. |
| 6,907,293 B2 | 6/2005 | Grill et al. |
| 7,187,977 B2 | 3/2007 | Paul, Jr. |

(Continued)

FOREIGN PATENT DOCUMENTS

| | | |
|---|---|---|
| WO | 01/51122 A1 | 7/2001 |
| WO | 20081004204 A1 | 1/2008 |
| WO | 20101014260 A1 | 2/2010 |

OTHER PUBLICATIONS

Bouhassira, D. et al., "Prevalence of chronic pain with neuropathic characteristics in the general population," Pain, 2008, vol. 136, pp. 380-387.

(Continued)

*Primary Examiner* — Alyssa M Alter
(74) *Attorney, Agent, or Firm* — Tarolli, Sundheim, Covell & Tummino LLP (57) ABSTRACT

Methods of treating pain are disclosed, wherein a non-pulsed, low-frequency electrical current is applied to the nerve carrying the pain signals in order to suppress transmission of those signals. In desired embodiments, the current is applied in a direction transverse to the nerve axis. Such currents have been found not to induce motor-neuron recruitment, meaning these methods can treat pain without causing muscle spasm or other muscular responses. A cuff for applying such a current transverse to the nerve axis is also disclosed.

19 Claims, 10 Drawing Sheets

(56) References Cited

U.S. PATENT DOCUMENTS

| | | |
|---|---|---|
| 7,260,436 B2 | 8/2007 | Kilgore et al. |
| 7,389,145 B2 | 6/2008 | Kilgore et al. |
| 7,623,925 B2 | 11/2009 | Grill et al. |
| 2006/0052826 A1 | 3/2006 | Kim et al. |
| 2007/0021801 A1 | 1/2007 | Heruth et al. |
| 2007/0066971 A1 | 3/2007 | Podhajsky |
| 2007/0167992 A1 | 7/2007 | Carley |
| 2007/0191709 A1 | 8/2007 | Swanson |
| 2007/0213783 A1* | 9/2007 | Pless ............................ 607/42 |
| 2007/0265691 A1 | 11/2007 | Swanson |
| 2007/0293915 A1 | 12/2007 | Kilgore et al. |
| 2008/0027506 A1 | 1/2008 | Cuozzo |
| 2008/0172116 A1 | 7/2008 | Mrva et al. |
| 2008/0183258 A1 | 7/2008 | Inman |
| 2008/0228250 A1 | 9/2008 | Mironer |
| 2008/0288019 A1 | 11/2008 | Heller |
| 2008/0294221 A1 | 11/2008 | Kilgore et al. |
| 2009/0036945 A1 | 2/2009 | Chancellor et al. |
| 2009/0099439 A1 | 4/2009 | Barolat |
| 2010/0030310 A1 | 2/2010 | Feler et al. |
| 2010/0057162 A1 | 3/2010 | Moffitt et al. |
| 2010/0057163 A1 | 3/2010 | Moffitt et al. |
| 2010/0057164 A1 | 3/2010 | Moffitt et al. |
| 2010/0057165 A1 | 3/2010 | Moffitt et al. |
| 2010/0057177 A1 | 3/2010 | Moffitt et al. |
| 2010/0094378 A1 | 4/2010 | Inui et al. |
| 2010/0100154 A1 | 4/2010 | Roche |

OTHER PUBLICATIONS

Ghoname, E.A. et al., "The Effect of Stimulus Frequency on the Analgesic Response to Percutaneous Electric Nerve Stimulation in Patients with Chronic Low Back Pain," Anesthesia & Analgesia, 1999, vol. 88, pp. 841-846.

Lertmanorat, Z. et al., "Electrode Array for Reversing the Recruitment Order of Peripheral Nerve Stimulation: Experimental Studies," Annals of Biomedical Engineering, Jan. 2006, vol. 34, No. 1, pp. 152-160.

Torrance, N. et al., "The Epidemiology of Chronic Pain of Predominantly Neuropathic Origin: Results From a General Population Survey," The Journal of Pain, Apr. 2006, vol. 7, No. 4, pp. 281-289.

Yakovlev, A.E. et al., "Spinal Cord Stimulation as a Treatment Option for Intractable Neuropathic Cancer Pain," Clinical Medicine & Research, Dec. 2008, vol. 6, No. 3/4, pp. 103-106.

International Search Report and Written Opinion issued Dec. 12, 2011 in PCT Application No. PCT/US11/47190.

Extended European Search Report issued in corresponding European Patent Application No. 11816962.2 on Dec. 10, 2013.

* cited by examiner

Sinusoid waveform:

Exponential waveform:

Triangle waveform:

Mixed logarithmic waveform:

Logarithmic waveform:

Mixed exponential waveform:

Fig. 12

METHOD TO TREAT PAIN THROUGH ELECTRICAL STIMULATION OF NERVES

CROSS-REFERENCE TO RELATED APPLICATIONS

The present application claims the benefit of U.S. provisional patent application Ser. No. 61/372,341 filed Aug. 10, 2010, which is incorporated herein by reference in its entirety.

BACKGROUND

1. Field of the Invention

The present invention relates generally to the treatment of pain. More particularly, it relates to the treatment of pain through electrical nerve stimulation.

2. Description of Related Art

Neuropathic pain is a potentially debilitating symptom arising from a wide variety of causes including diabetes, amputation, various malignant and benign cancers, certain infectious diseases and hereditary conditions. This pain is often progressive and generally due to direct cellular damage or impingement of peripheral nerve tissues. It is typically treated with non-steroidal anti-inflammatory drugs, opioids, anticonvulsants and antidepressants. However, many cases are not well controlled on any of these medications. Even for cases where these drugs are effective, finding the correct drug and dose is often a long and intensive procedure of trial and error.

Neuropathic pain is an extremely common disorder. According to a French study [1] it is estimated that 6.9% of the population suffers from neuropathic pain and in 5.1% of the population the pain is moderate to severe. A separate British study [2] estimated the size of the affected population closer to 8%. It is further estimated that 10% to 15% of these patients do not respond to conventional treatments [3]. Alternative treatments that inhibit or prevent the transmission of pain signals through the nerves that carry them would be desirable.

Nerves are made up of bundles of nerve fibers called fascicles, which are bound by perineurium membranes. Each fascicle contains a large number of fibers of different sizes (diameters) and having different functions (motor, sensory, pain-transmitting, etc.). Some of the fibers within the fascicles have a myelin sheath coating the fiber, which produces faster signal-transmission rates through the fiber. Other fibers do not have a myelin sheath, resulting in slower signal-transmission rates. Larger, myelinated fibers (for example $A\alpha$- and $A\beta$-fibers) having diameters on the order of 10 µm typically are responsible for sensory and motor-control functions. Conversely, pain signals, such as those responsible for neuropathic pain, are transmitted via much smaller (diameters less than 1 µm), e.g. unmyelinated C-fibers, which can have diameters on the order of 0.1 µm or lower. To treat pain, it is desirable to inhibit the transmission of signals through the unmyelinated small fiber strands (such as C-fibers), while not substantially affecting the transmission characteristics of (or activating) the larger fibers responsible for motor control and other sensory functions.

Electrical stimulation of nerves carrying pain signals has been used to attempt to attenuate the sensation of pain. These include spinal cord stimulation (SCS), transcutaneous electrical stimulation (TENS), percutaneous electrical stimulation (PENS), and Peripheral Nerve Field Stimulation (PNFS). These techniques are thought to operate by inducing parasthesia, or a pins and needles sensation, which overwhelms much of the pain response but is not thought to inhibit transmission of the pain signals. The sensation of parasthesia simply masks the pain so it is less evident to the patient. But this effect can be reduced over time, as the patient becomes acclimated to the parasthesia and begins to notice once again the underlying pain. In addition, parasthesia itself can be unpleasant, and in some patients may actually exacerbate the perception of pain.

Current literature on blocking electrical nerve signals does not describe blocking signal-transmission through the smaller, unmyelinated C-fibers, but instead focuses on larger $A\alpha$ and $A\beta$ motor units. Moreover, the aforementioned techniques often cannot be focused on just the pain-signal carrying fibers, but instead also affect larger nerve fibers. As a result, using current techniques to induce parasthesia to mask the pain signals transmitted through small, unmyelinated fibers can undesirably affect the transmission characteristics of larger fibers responsible for higher sensory and motor functions, and even activate those fibers causing involuntary muscle contractions (spasm) and other sensory side effects. It is desirable to inhibit, e.g. block, the transmission of pain signals through the small, unmyelinated fibers that principally carry them. Ideally, this will be achieved without substantially affecting the larger fibers responsible for higher sensory and motor functions.

SUMMARY OF INVENTION

A method for treatment of pain is provided, which includes transmitting a non-pulsed electrical current through a portion of a peripheral nerve in a patient in need of such treatment, wherein the current has a frequency in the range of 10 to 2000 Hz.

A cuff for transmitting a current transverse to a nerve longitudinal axis is also provided. The cuff includes a substrate having a strip of dielectric material, and respective anode and cathode electrodes embedded in or laminated to said substrate. The electrodes are positioned on the substrate opposite one another with respect to a hinge portion of the substrate. The substrate is configured to bend at the hinge portion to enclose the nerve at a location where the cuff is applied so as to position the anode and cathode electrodes substantially diametrically opposed to one another about the nerve.

DETAILED DESCRIPTION OF PREFERRED EMBODIMENTS

As used herein when a range such as 5-25 (or 5 to 25) is given, this means at least 5 and, separately and independently, not more than 25.

It has been discovered that transmitting an electrical current having a non-pulsed (preferably charge-balanced) waveform through a nerve at low frequency can inhibit or block the transmission of pain signals through unmyelinated C-fibers. The low frequency mentioned above is desirably selected in the range of 10-2000 Hz, more preferably 10-500 Hz. In preferred embodiments, the frequency is in the range of 10-300 Hz, 10-200 Hz, 50-180 Hz, 75-150 Hz or 100-150 Hz, preferably of or about 130 Hz. It has been discovered that non-pulsed currents at such low frequencies can inhibit the transmission of pain signals through C-fibers. As used herein, a non-pulsed waveform is one that exhibits a slow rise time such that there is a delay between its zero and peak amplitudes; i.e. the waveform does not reach peak amplitude from neutral in a single discrete step. A non-pulsed electrical current is one that includes a series of non-pulsed waveforms; preferably it has only non-pulsed waveforms. Analog waveforms are preferred, wherein the electrical current exhibits at least 10 μs to reach its peak amplitude from neutral (zero current). Preferably, an analog waveform exhibits at least 20 μs to reach its peak amplitude from neutral. Alternatively, digital waveforms may be used to achieve a delayed rise time (e.g., for at least the aforementioned time periods) through a series of discrete steps from zero to peak amplitude, the sum of which constitute a slow rise that approximates an analog waveform. However, such a digital waveform may be less preferred for the reasons set forth in the next paragraph. Assuming the waveform includes both cathodic and anodic portions (e.g., if it is charge balanced), preferably both the cathodic and anodic portions of the waveform exhibit the aforementioned non-pulsed characteristics. Note that even for charge-balanced waveforms, the anodic and cathodic portions need not possess the same shape—i.e. they need not be mirror images of one another.

Non-pulsed (particularly analog) waveforms are inefficient to activate larger nerve fibers, such as Aα and Aβ motor units. Activation of such larger fibers is most efficiently achieved via fast-rise waveforms, wherein the delay from zero to peak amplitude is minimized or instantaneous. Consequently, a non-pulsed waveform as herein described is less likely to activate larger nerve-fiber units responsible for motor and other higher sensory functions, while nevertheless effectively targeting C-fibers to inhibit or block the transmission of pain signals. To the extent motor fibers may be activated, it will be to a lesser extent compared to conventional therapies using similar currents in a pulsed mode. While a digital non-pulsed waveform as above described may be used, because it is technically the sum of numerous discrete (instantaneous) current steps, such a waveform may have a greater potential to induce a response in larger, myelinated fibers. This potential may increase as the amplitude of the electrical current waveform is increased. The potential for large nerve-fiber activation should be further minimized via a transverse application of the electrical current (described below), which may render the use of digital non-pulsed waveforms to be less of a concern.

It should be noted that in the range of 20-40 Hz, the applied electrical current has the greatest potential to induce muscle contractions by activating large motor-unit fibers in the treated nerve if a waveform having a relatively fast rise time is used. If a frequency in this narrow range is to be used, the rise time should be at least 1000 μs to minimize the potential for or magnitude of motor-unit activation. However, a transverse application of the electrical current (described below) may minimize or even prevent the potential for motor-unit activation, even at frequencies of 20-40 Hz. The inhibitory effect of transverse current application in this or other frequency range(s) on motor-unit activation may depend, in part, on the amplitude (power) of the current waveform selected. It is anticipated that a certain amount of trial-and-error may be useful to avoid undesirable or impermissible motor-unit activation; but such will be well within the capability of one having ordinary skill in the art.

Figure 12:
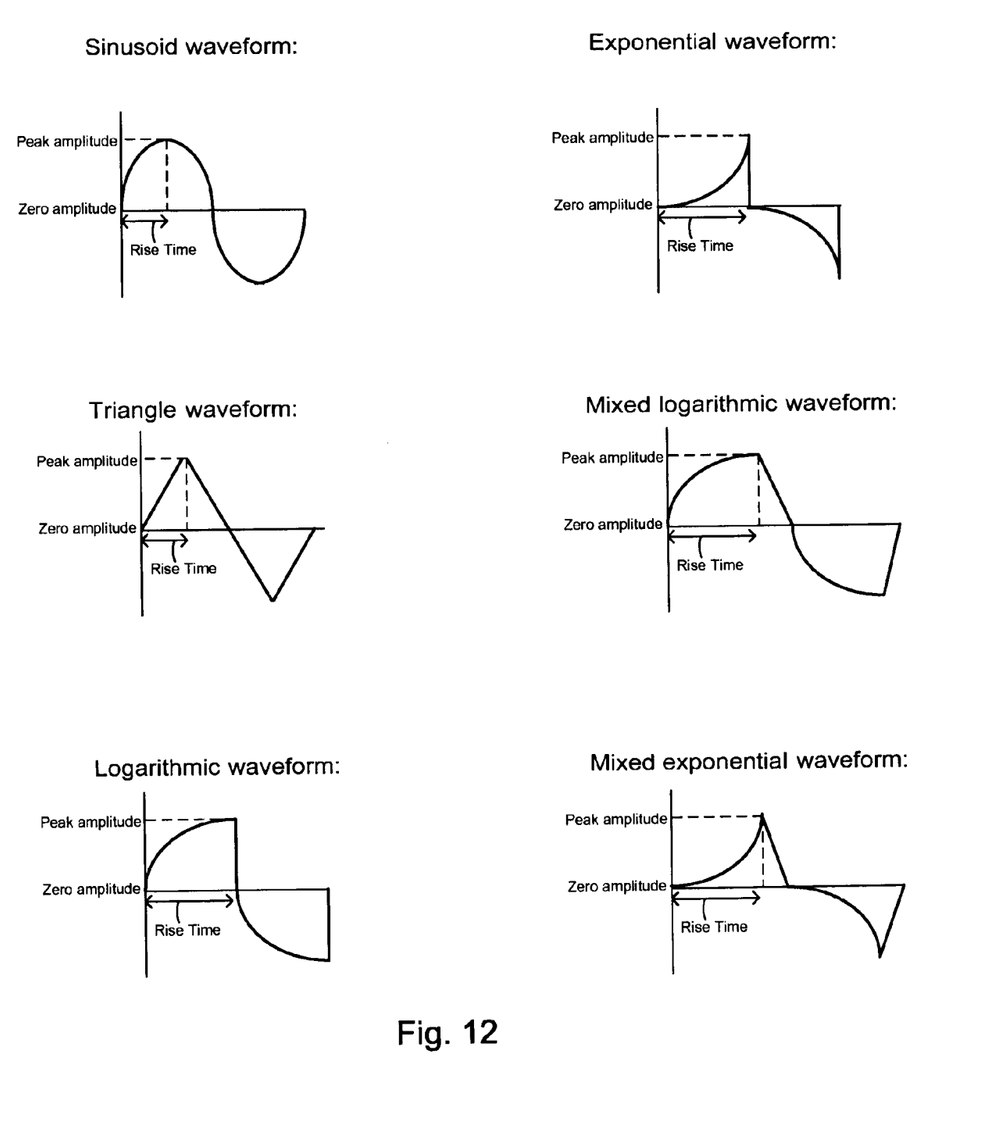
FIG. 12 illustrates several non-limiting examples of non-pulsed waveforms.

A sinusoid waveform is one that has been found useful in the disclosed methods, as seen in the Examples below. However, other non-pulsed waveforms also may be used, as shown in FIG. 12. For example those having a linear but non-instantaneous rise time from zero to peak amplitude in one or more segments (e.g. a triangular, trapezoidal or other polygonal waveform) may be useful in practicing the disclosed methods. Alternatively, waveforms having exponential or logarithmic rise from zero to peak amplitude also may be employed. In further embodiments, waveforms employing combinations of the foregoing between zero and peak amplitude for at least one (and preferably both) of the cathodic and anodic portions of the waveform may be used. Several exemplary non-pulsed waveforms meeting the aforementioned criteria are illustrated in FIG. 12.

Note that a non-pulsed waveform as used herein need not have a slow decline for either the cathodic or anodic portions of the wave. For example, both the logarithmic and exponential non-pulsed waveforms illustrated above have a slow-rise for both the cathodic and anodic portions of the wave, but an instantaneous step from peak amplitude to zero (neutral) for the declining segment.

A current amplitude in the range of greater than 0.4 up to 5 mA may be preferred, and has been used to good effect in conjunction with a sinusoidal waveform. Other amplitudes or amplitude ranges may be optimized in view of the present disclosure based on the particular waveform selected. Ideally, the stimulation amplitude will be greater that the threshold for pain block by suppressing or inhibiting pain-signal transmission through C-fibers, but smaller that the threshold for large motor- or sensory-fiber activation.

The methods disclosed herein are applicable to inhibit or block the transmission of pain signals through C-fibers in peripheral nerves. Notably, the application of non-pulsed electrical currents in the frequency ranges disclosed above does not merely overwhelm or mask the pain response via parasthesia as in conventional treatments. Rather, it suppresses the pain response.

As noted above, ideally these methods will have minimal effect on larger, myelinated fibers. Preferably, the disclosed methods are targeted to selectively inhibit the transmission of pain signals through C-fibers, while having minimal effect on the transmission characteristics, and minimizing activation, of larger fibers such as motor units. It has been discovered that application of the disclosed electrical currents in a direction transverse to the nerve longitudinal axis can have the effect of inhibiting pain-signal transmission through the small C-fiber strands without substantially affecting the transmission characteristics of larger fibers, or at least affecting them to a lesser extent than conventional therapies. As used herein, 'transverse to the nerve longitudinal axis' refers to the transmission of an electrical current through a nerve in a direction that is perpendicular to at least one plane containing the longitudinal axis of the nerve at the location where the electrical current is applied. In preferred embodiments, the transversely-directed current is applied diametrically through the nerve, such that at least a component of the current (preferably the predominant component) travels along a path substantially intersecting and perpendicular to the longitudinal axis of the nerve.

As will be seen in the Examples below, the application of an electrical current as herein described in the transverse direction has been shown to inhibit or even prevent the transmission of pain signals through C-fibers while having minimal effect on larger motor units. This is a particularly surprising result because it was not previously recognized that a transversely-applied current (conventionally believed to have little or no effect on nerve fibers) could effectively inhibit the transmission of pain signals through unmyelinated C-fibers. The present embodiments take advantage of the conventional wisdom regarding transversely-applied currents (that they have little or reduced or negligible effect on the transmission or activation characteristics of nerve bundles), as well as the discovery that such currents in fact can inhibit or even block the transmission of pain signals in unmyelinated C-fibers, to selectively treat pain while minimizing or preventing side effects associated with the activation of motor and higher-sensory fibers.

To apply the transverse electrical current to a peripheral nerve, it is desirable to employ a bipolar electrode design, with opposite-pole electrodes (anode and cathode) disposed at diametrically opposed locations about the nerve trunk, both at substantially the same axial location. Ideally, the electrodes are configured to ensure as much as possible an electrical current between them (and through the nerve) having transverse field lines, while minimizing to the greatest extent possible the incidence of longitudinal field lines, or field lines having a longitudinal component. This is because the smaller the longitudinal component of the applied electric field, the less motor recruitment will result. One way to produce a transverse electric field is to employ substantially planar anode and cathode electrodes, parallel to one another at diametrically opposed locations about the nerve. In a preferred embodiment, the respective electrodes are recessed into a dielectric material, e.g. silicone, to minimize as much as practical the incidence of fringe effects when energized.

Figure 1:
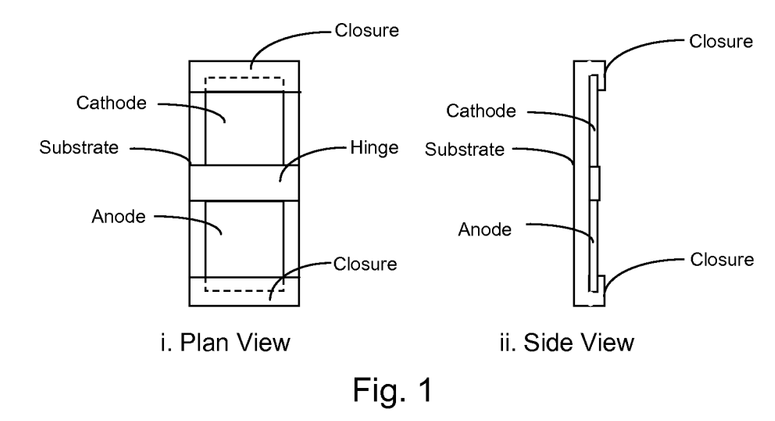
FIG. 1 is a schematic illustration (both plan and side views) of a nerve cuff having electrodes for applying current to a nerve in a direction substantially transverse to the longitudinal axis of the nerve.

According to one design, the anode and cathode electrodes may be provided in a cuff that is fashioned and dimensioned to fit about the circumference of the nerve to be treated; i.e. so that the nerve can be enclosed by the substrate at the location where the cuff is applied. The cuff can be fabricated initially as a flat longitudinal strip of dielectric material forming a substrate, and having respective anode and cathode electrodes embedded therein as illustrated in FIG. 1. Alternatively, the electrodes can be laminated to the surface of the substrate.

Figure 2:
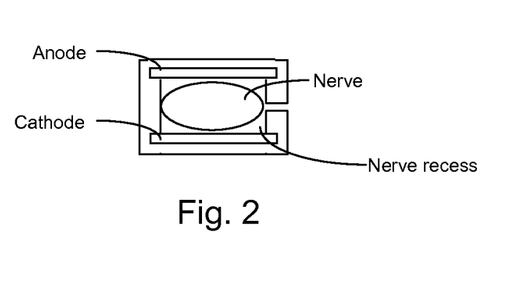
FIG. 2 is a schematic illustration of the cuff of FIG. 1, in section, closed around a nerve with the diametrically opposed anode and cathode electrodes aligned to deliver a current to the nerve in a direction substantially transverse to its longitudinal axis.

The substrate can be any suitable biocompatible material that is dielectric and suitably flexible to bend at the hinge so that the opposed closure portions can be secured together to close the cuff about a nerve as shown in FIG. 2.

For example, the substrate may be made of silicone. The electrodes can be metallic, such as metallic foil, for example platinum, gold, copper or other suitably conductive metals. More nonreactive metals such as platinum and gold are preferred to avoid undesirable reactions with body materials, as well as oxidation, when implanted in vivo. As mentioned above and seen in the schematic illustrations at FIG. 1, the electrodes are recessed in the dielectric substrate material, both to provide a recess to accommodate the nerve extending through the cuff in the closed condition (FIG. 2), as well as to embed the edges of the electrodes in the dielectric material to minimize fringe effects. The nerve recess of the above-illustrated nerve cuff could be filled with an anisotropic material to make the resulting electric field more uniform.

Figure 3:
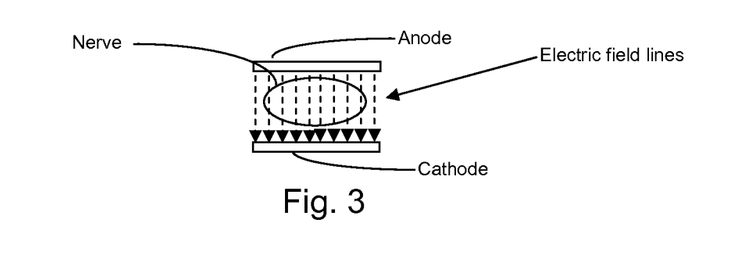
FIG. 3 illustrates the electric field lines resulting from application of a current to a nerve using the cuff in FIGS. 1 and 2, substantially transverse to the longitudinal axis of the nerve.

Except as otherwise indicated, the figures herein are not necessarily drawn to scale (including individual elements therein with respect to one another), other than to illustrate that the anode and cathode are arranged diametrically opposite one another relative to a nerve between them when the cuff is closed about the nerve. As noted above, the anode and cathode are preferably substantially planar. The parallel, planar arrangement of electrodes illustrated in FIG. 2 will produce field lines predominantly as illustrated in FIG. 3, wherein the field lines are substantially parallel to one another, and extend in a common transverse direction relative to the nerve axis.

It is recognized that some curvature of the electrodes may result about an axis parallel to the nerve longitudinal axis as the cuff is wrapped circumferentially about the nerve. Some such curvature is acceptable because the resulting field lines still will be predominantly transverse to the nerve longitudinal axis similarly as in FIG. 3. To minimize or inhibit excessive curvature, a stiffener can be incorporated into the cuff, for example. A preferred stiffener is a multi-layer sheet made of a biocompatible polymer embedded within the cuff top and bottom section.

The electrodes utilized in the present methods preferably have lateral dimensions (perpendicular to the longitudinal axis of the target nerve) that extend to or beyond the normal width of the nerve to be treated. Ideally, the cross-sectional area of the nerve will be the same or slightly smaller than the cross-sectional area of the electrode, with the electrode having a smaller opening height. This reshapes the nerve in a flatter configuration allowing better control of the field lines from stimulation. Should the cross-sectional area of the cuff be smaller than the nerve, the nerve will be compressed and damage may result. Electrodes that have very small widths or those with larger opening heights will tend to generate a more non-uniform current field in the vicinity of the nerve, having a larger longitudinal component that will be more likely to activate motor-fiber axons. It is desirable that the anode and cathode have the same dimensions.

To apply the current, the electrodes each can be connected via a respective lead wire to a power supply that applies a voltage or a current source to induce an electrical field between them of the desired amplitude. The power supply may include circuitry to produce or convert the current in the desired waveform, e.g. a non-pulsed waveform as described above. In a preferred embodiment, the power supply includes a battery that is implanted in the patient proximate the treatment site. The power supply can incorporate or be associated with circuitry capable to monitor the electrode, the induced electric field through the nerve at the treatment site, and any response (or signal suppression) in the nerve; e.g. to monitor motor-fiber recruitment and/or C-fiber signal suppression. Relevant data regarding the electrode performance and nerve response can be transmitted via a telemetry signal to a receiver outside the body. Said receiver may be equipped to transmit a control signal to implanted control circuitry, incorporated in or coupled to the power supply, to actuate the implanted electrode based on telemetry data that is received, or based on a manual user input.

Application of the electrodes is not limited to the use of the cuff as above described. Electrodes may be fixed in diametrically-opposed position relative to the nerve to be treated via other suitable techniques. For example, individual electrodes may be glued via suitable biocompatible adhesives to the nerve trunk. In a further alternative, a cuff may be used, which is not manufactured initially as a flat silicone substrate but instead has three-dimensional structure adapted to fit over the nerve. Alternative structures for fixing the electrodes in place could be devised by those having ordinary skill in the art to practice the methods disclosed herein.

In addition, electrode structures other than the transverse electrodes described above also could be used. For example, strips of conductive material could be used (for example with individually balanced current sources), as well as electrodes arranged as concentric rings. The position of each electrode could be adjusted to generate longitudinal electrical fields that minimize activation of large fibers (electrode separation distance as small as the distance between the nodes of Ranvier for larger fibers (100 um)) [4].

The electrodes or electrode cuff disclosed herein can be applied over the desired peripheral nerve via a surgical procedure. The surgical procedure can be an outpatient procedure utilizing microsurgery, or it could be performed via a minimally-invasive technique (laparoscopic surgery) depending on the particular nerve to be targeted, its location and the presence of potentially complicating obstacles nearby. More invasive surgical procedures may be used at the discretion of the attending surgeon, if they are appropriate. The particular surgical procedure for implanting the electrode cuff is not critical to the methods disclosed herein, and appropriate surgical procedures will be well within the capability of a qualified physician or surgeon to select.

The electrodes described herein can be used alone to deliver a current to a target nerve in order to inhibit or even block pain-signal transmission through C-fibers while minimizing or substantially avoiding activation of larger nerve fibers that may result in spasm or other higher sensory side effects. Alternatively, the methods disclosed herein could be used in combination with the longitudinal electrical stimulation (e.g. pulsed) of the nerve in the same vicinity to simultaneously treat pain and selectively stimulate a desired motor response without interference from the stimulation responsible for pain treatment. Also, very high frequency stimulation (VHFS) above 10 kHz may be combined with these therapies to provide both motor and pain block.

The following examples further illustrate aspects of the disclosed methods. They are provided by way of illustration only and not limitation.

EXAMPLES

Example 1

The Sural-Gastrocnemius reflex in rabbits can be elicited by stimulating the sural nerve and measured as an EMG twitch in the Gastrocnemius muscle. This reflex is amplified by pain signals (e.g. heat applied to the skin on the heel), as indicated by a large increase in the amplitude of the reflex. A series of experiments were conducted in a rabbit model to measure the effectiveness of treating pain through application of a non-pulsed, low-frequency electrical current across the sural nerve in a direction transverse to the nerve longitudinal axis. In a first set of experiments, the efficacy of this treatment was measured utilizing the application of heat to generate the pain signal. A number of trials were conducted under a series of four conditions: electrical stimulation to elicit a motor reflex response; the application of that stimulation combined with application of heat to the skin of the rabbit heal; application of a non-pulsed, 130 Hz sinusoidal current transverse to the sural nerve, without other stimuli; and finally application of the same non-pulsed, 130 Hz current together with the application of heat to the rabbit heal to induce a pain signal. The current utilized in these experiments was 800 μA. The non-pulsed current was applied via a nerve cuff such as that described above with respect to FIGS. 1-3 applied to the sural nerve proximate the rabbit heel. Reflex stimulus was applied via a different set of electrodes applied to the sural nerve more distal from the rabbit heel. EMG twitch response was recorded via recording leads attached to the sural nerve between the transverse cuff and reflex electrodes.

Figure 4:
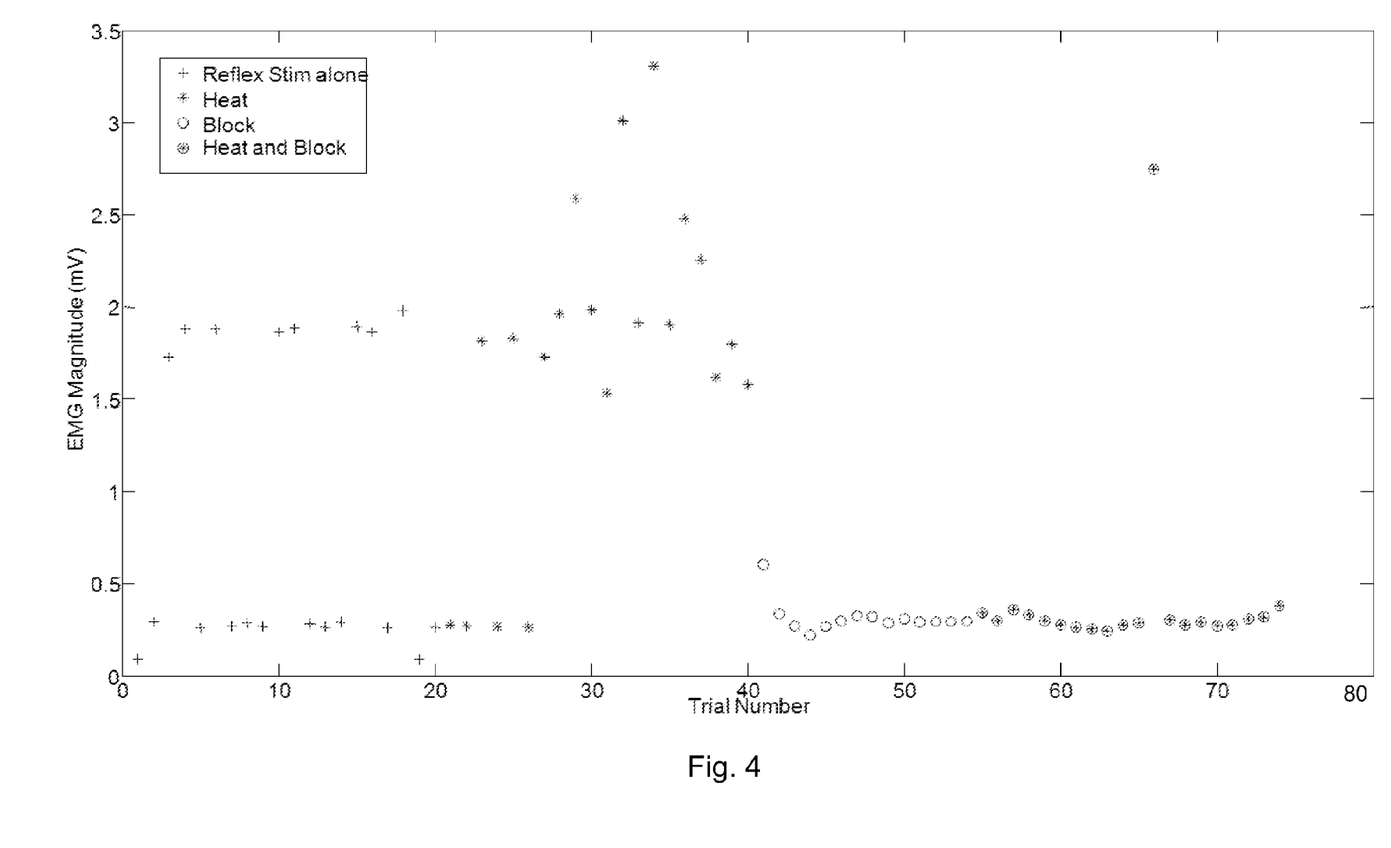
FIG. 4 is a plot showing EMG twitch response measured in the rabbit sural nerve in response to a variety of stimuli for a number of trials as described in Example 1. These data indicate effective blockage of pain-signal transmission through the nerve based on heat applied to the rabbit heel, via application of a transverse, 130 Hz and 800 µA electrical current to the nerve proximate the heel.

As seen in FIG. 4, the series of trials under the first set of conditions (reflex stim alone) predominantly produced either baseline EMG signals or elevated EMG signals consistent with the Sural-Gastrocnemius reflex—magnitude ~1.7 to 2 mV in FIG. 4. The addition of heat in the second set of trials (heat) elicited the predicted EMG-signal amplification as noted above, with measured EMG magnitudes consistently above 1.5 mV (with numerous well about 2 mV) except for the first four of these trials. It is possible that in these trials application of heat had not been long enough to elicit a pain response. In the third set of trials (block), the heat was removed and the 130 Hz non-pulsed and transversely-applied current was applied and allowed to set in for one minute before the reflex was tested again. As seen in FIG. 4, this current elicited essentially no EMG response above baseline, suggesting that this current does not itself affect the amplitude of the reflex; i.e. does not induce motor-unit recruitment that would produce a physical reflex. These results confirm that transverse application of an electrical current across a nerve, at least at the low frequencies contemplated herein, does not produce large-scale motor-unit recruitment. Finally, in the fourth set of trials (heat and block) it is seen that with the non-pulsed, low-frequency current applied as above described, the EMG response remained essentially at baseline despite the simultaneous application of heat to induce a pain signal in the sural nerve. The zero or negligible deviation from baseline in this fourth set of trials suggests that the applied transverse current effected a complete block of the pain signal produced through the application of heat to the rabbit heel.

Preliminary data suggest that an electrode cuff employing cathode and anode to apply a transverse current through a sensory nerve as described above can provide an efficient pain block compared to a conventional tripolar FINE-type electrode, but that it has at least 3 times greater threshold for motor-fiber stimulation compared to the FINE-type electrode.

Figure 7:
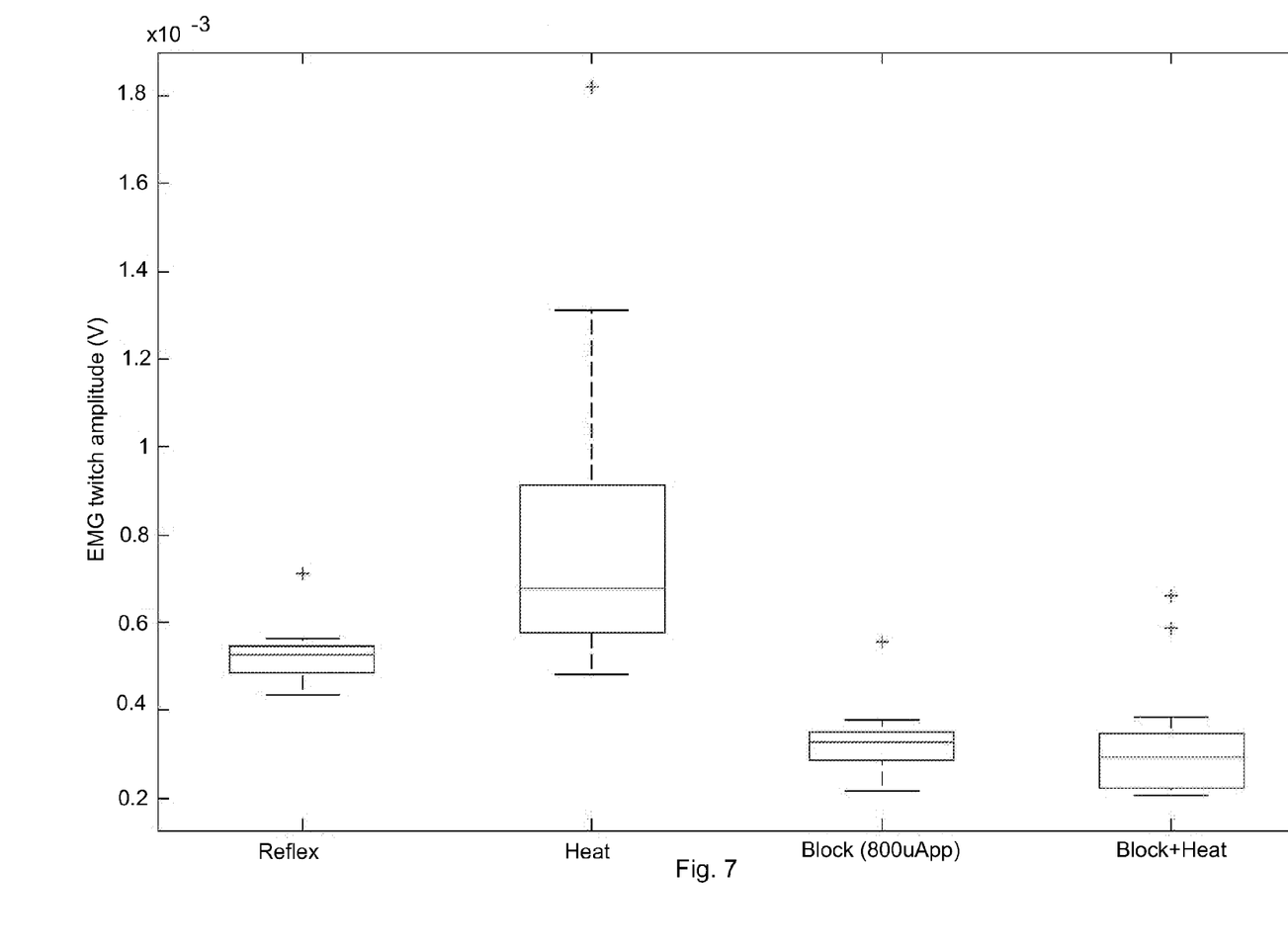
FIG. 7 is a statistical analysis of the data in FIG. 4 for Example 1, showing the baseline level of the Sural-Gastrocnemius reflex utilized in the example (Reflex), the heat-induced amplification of the reflex (Heat), a small decrease in reflex baseline when the transverse current was applied to the sural nerve (Block), and no significant change in reflex activity when heat was applied at the same time as the transverse current to the sural nerve (Block+Heat).

FIG. 7 presents a statistical analysis based on measurements during the experiments described in this example (which are plotted in FIG. 4). The analysis shown in FIG. 7 further indicates that an effective pain block was achieved based on the methods employed in this example.

Example 2

Figure 5:
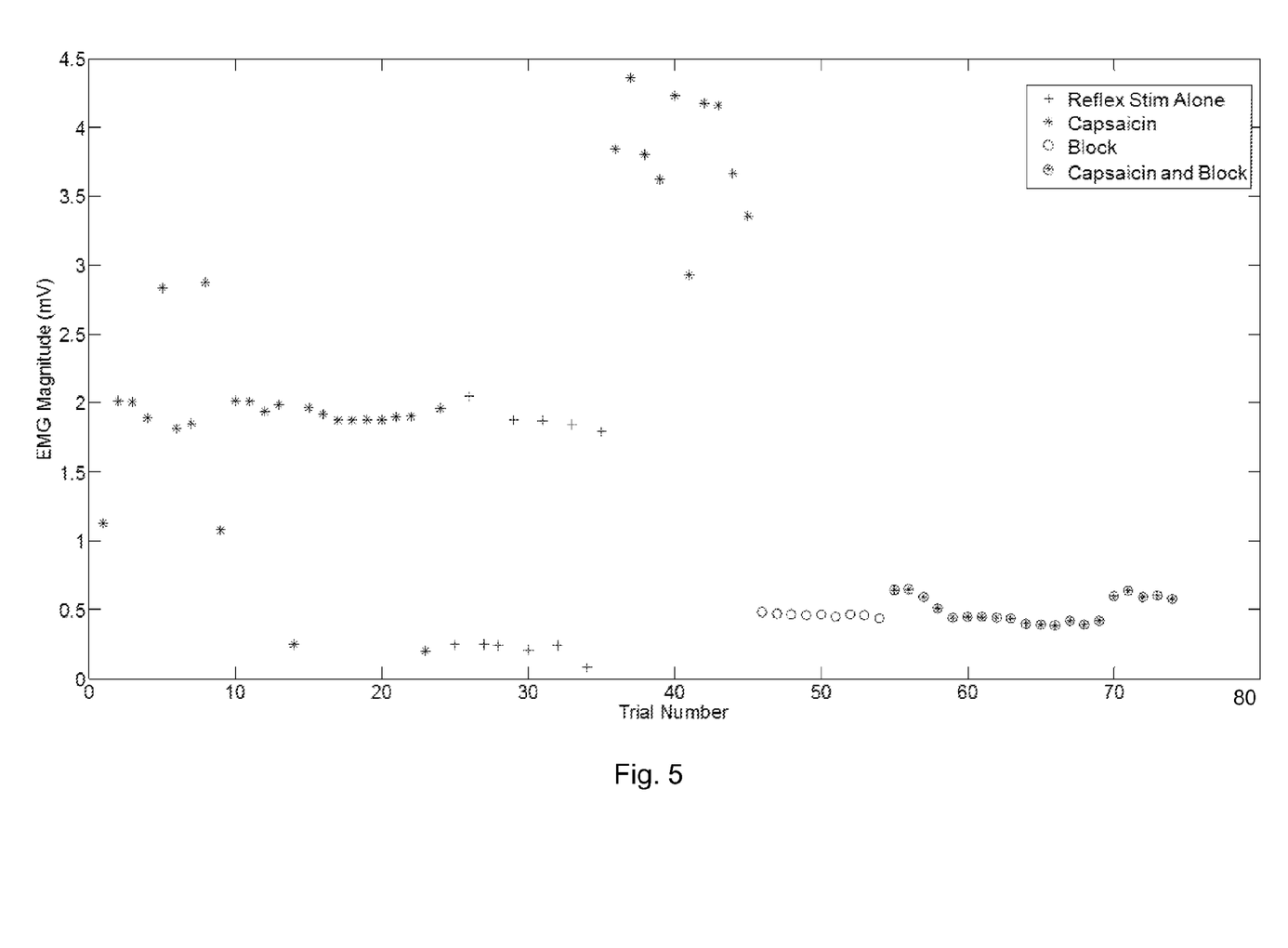
FIG. 5 is a plot similar to that in FIG. 4 for a number of trials as described in Example 2, wherein capsaicin (not heat) was applied to the rabbit heel to induce the pain response. These data likewise indicate effective blockage of pain-signal transmission through the sural nerve.

A second set of experiments was also conducted similar to those in Example 1 above, except this time capsaicin applied to the rabbit heel was used to induce the pain signals in the sural nerve. This set of experiments yielded remarkably similar results (data shown in FIG. 5). As in Example 1, the transversely-applied 130 Hz non-pulsed current essentially blocked the pain signal resulting from capsaicin application at the rabbit heel. These results confirm that the pain signals are indeed carried by C-fibers, and that application of a transverse, non-pulsed, low-frequency current as herein disclosed is an effective treatment to inhibit (and in the experiments of Examples 1 and 2, essentially block) the transmission of pain signals through those fibers.

Comparative Example 1

Figure 6:
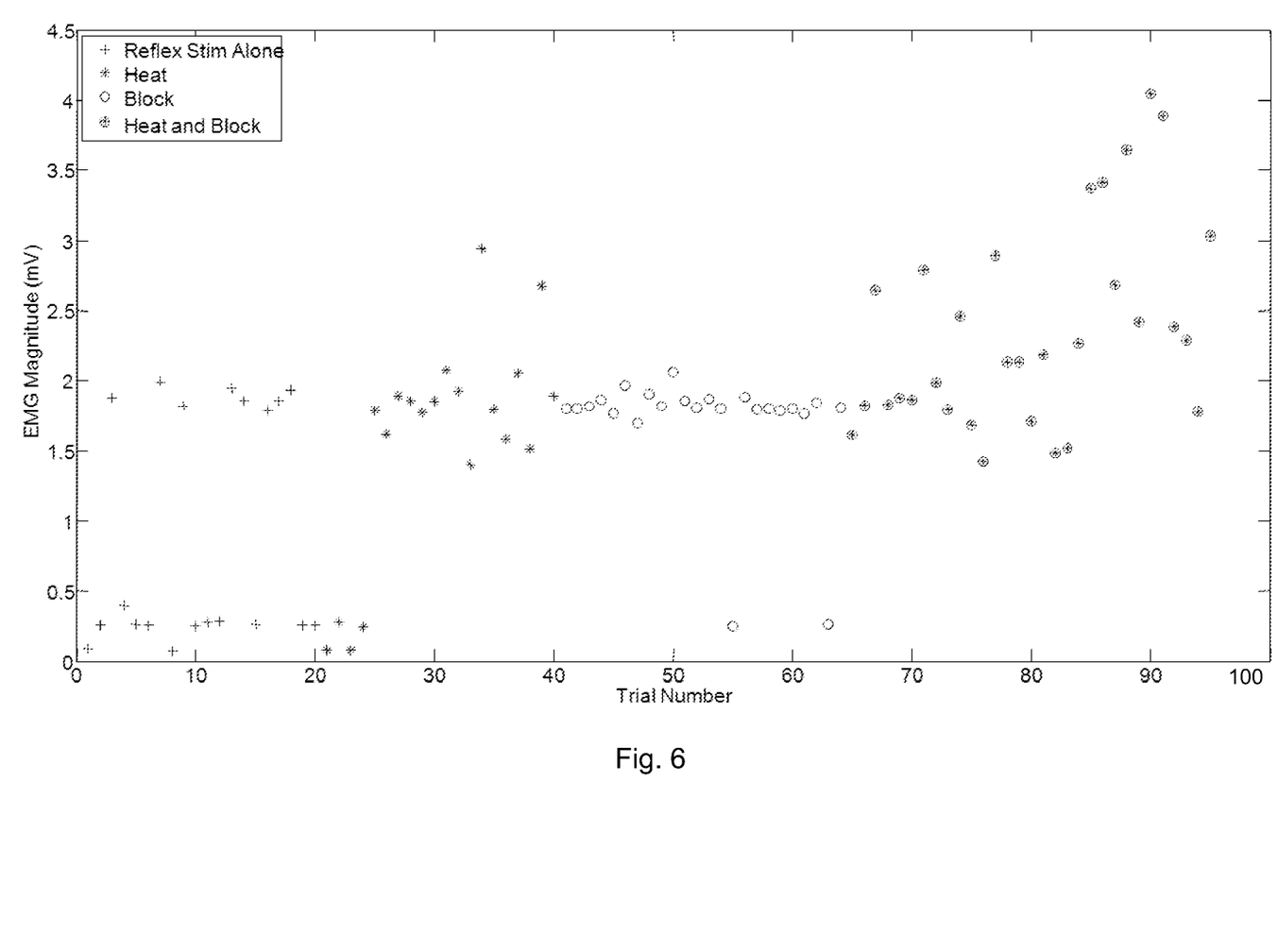
FIG. 6 is a plot similar to those in FIGS. 4 and 5 for a number of trials as described in Comparative Example 1, wherein heat was used to induce the pain response and a higher current frequency of 10 kHz was utilized instead of 130 Hz. These data indicate that the elevated current frequency of 10 kHz was ineffective to attenuate the pain-signal resulting from heat application to the rabbit heel.

Similar experiments as in Example 1 were carried out, the only difference being that the non-pulsed, transverse current used had a high frequency of 10 kHz (10,000 Hz). The results are plotted in FIG. 6, wherein it is seen that the 10 kHz current (block) did not attenuate the pain response induced by heat. These results demonstrate that such high frequencies are not effective to attenuate the pain response using the disclosed methods.

Example 3

Figure 8:
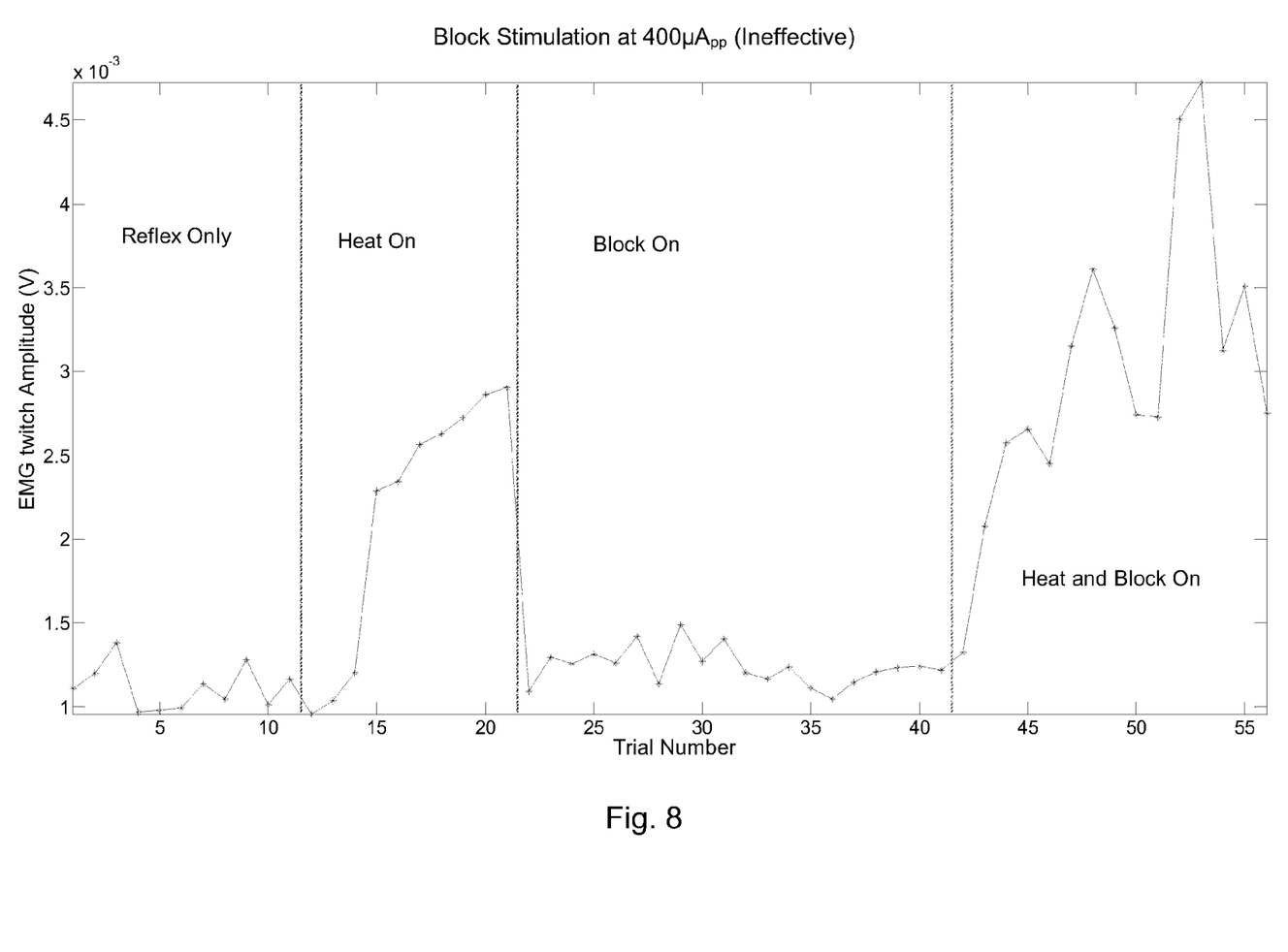
FIGS. 8 and 9 show respective plots of EMG twitch-response data for a series of experiments as described in Example 3, wherein transverse currents of 400 μA and 1 mA (1000 μA), respectively, were tested to determine their relative efficacy at attenuating pain signals in the rabbit sural nerve induced by application of heat to the rabbit heel.
Figure 9:
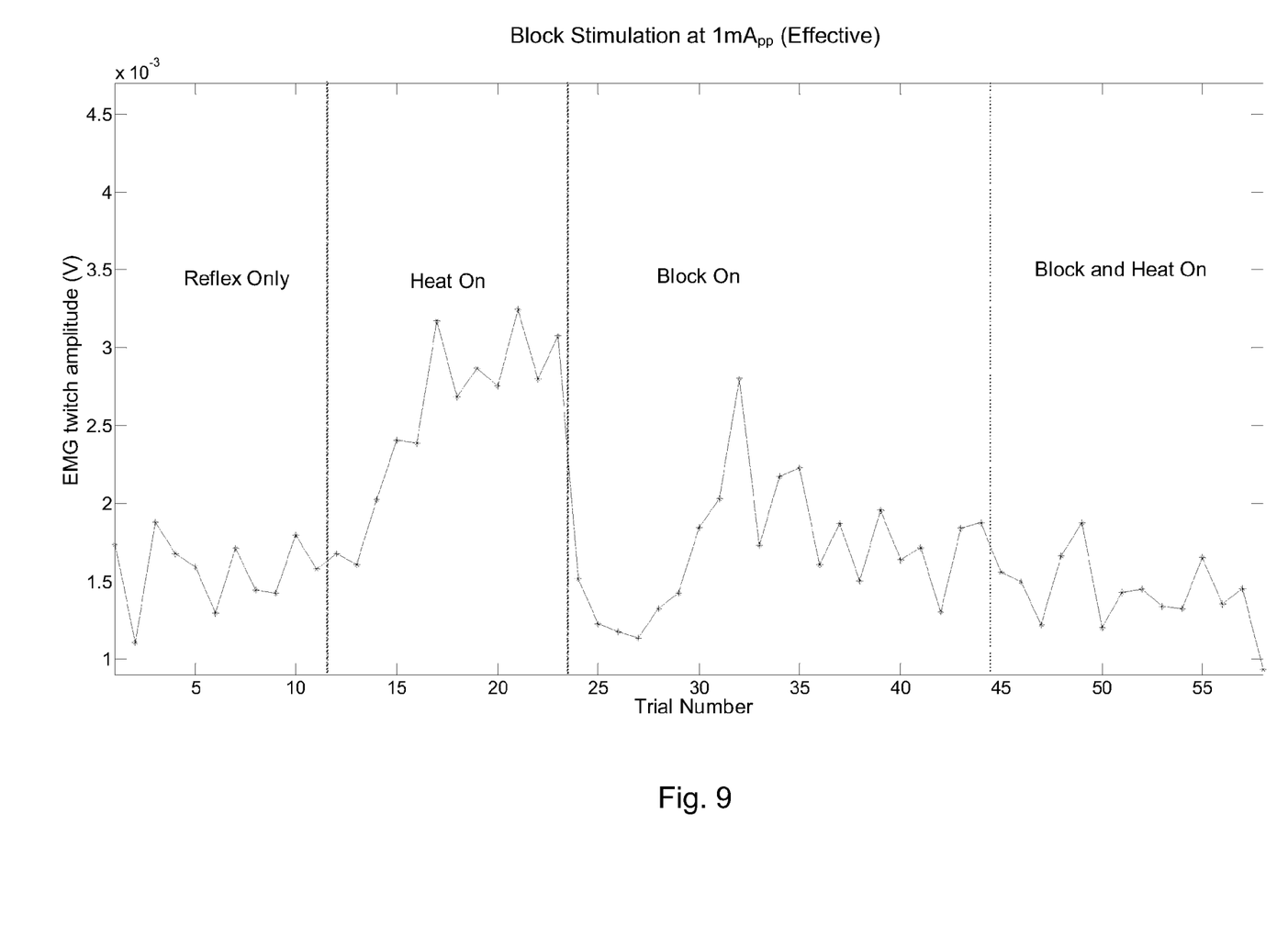

A further set of experiments were conducted to demonstrate the efficacy of the disclosed methods to attenuate pain signals in the sural nerve. FIGS. 8 and 9 show respective plots of EMG twitch-response data based on the same series of four conditions discussed above in Example 1. The differences from Example 1 were that the currents were applied longitudinally along the nerve axis as opposed to transversely, and in FIG. 8 the current was a 400 µA current while in FIG. 9 it was a 1 mA (1000 µA) current. Otherwise, the conditions of these experiments were the same as in Example 1.

As seen when comparing FIGS. 8 and 9, the 400 µA current was too low a magnitude to inhibit the transmission of pain signals through the C-fibers of the sural nerve. In fact, in at least some trials the pain signal seems to have been intensified compared to just "Reflex+Heat" alone. Conversely, when the 1 mA current was used the EMG twitch signal reflected essentially the baseline condition, indicating an effective block similar to the results obtained in Example 1.

Example 4

Figure 10:
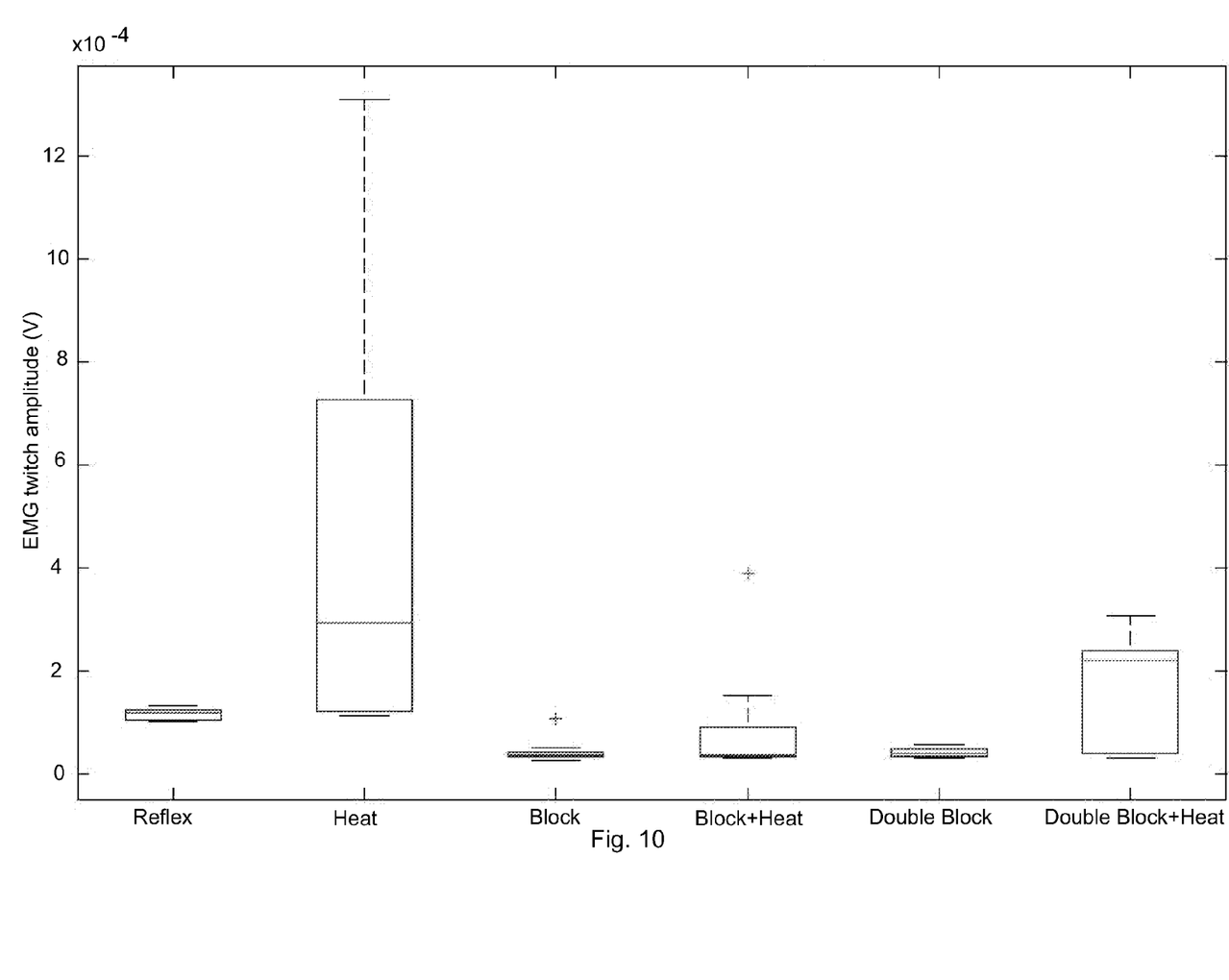
FIG. 10 is a histogram plotting statistical data obtained from experiments described in Example 4 to demonstrate the efficacy of utilizing a non-pulsed, low-frequency current to attenuate pain-signal transmission at the same time as utilizing a high-frequency current to suppress motor-neuron recruitment in the sural nerve.

A further experiment was conducted to determine the effectiveness of combining a 130 Hz current to suppress pain-signal transmission through C-fibers with a 40 kHz current to suppress transmission of motor signals through larger motor-fibers. In this experiment, both currents were applied longitudinally along the nerve axis. Both currents were applied via electrodes spaced longitudinally along the sural nerve, with the pair of electrodes for delivering the 130 Hz current positioned more proximate the rabbit heel, and the pair of electrodes for delivering the 40 kHz current located adjacent but spaced a short distance from the other pair. Both currents were applied at 800 µA. The data for this experiment are summarized in the histogram at FIG. 10. Those data show that for the "Block+Heat" (corresponding to application of the 130 Hz current+heat) and the "Double Block+Heat" (corresponding to the application of both currents+heat) measurements, the EMG twitch amplitude was lower than that for "Heat" alone. This evidences effectiveness at blocking pain-signal transmission both when the longitudinal 130-Hz current was applied alone and when it was applied in conjunction with the 40 kHz motor-blocking current. In addition, this experiment demonstrated that the inhibition of pain signals through C-fibers was due to the applied 130 Hz current, and not the 40 kHz current that was effective for motor-neuron blocking.

Example 5

A further experiment was conducted to compare the EMG twitch response produced from a 1 Hz pulse effective to induce motor recruitment in large nerve fibers with the combination of the same 1 Hz pulse and a longitudinally-applied 130 Hz sinusoid wave current. The same rabbit Sural-Gastrocnemius reflex model utilized in the prior examples was utilized in this experiment. EMG twitch response data are plotted in FIG. 11.

Figure 11:
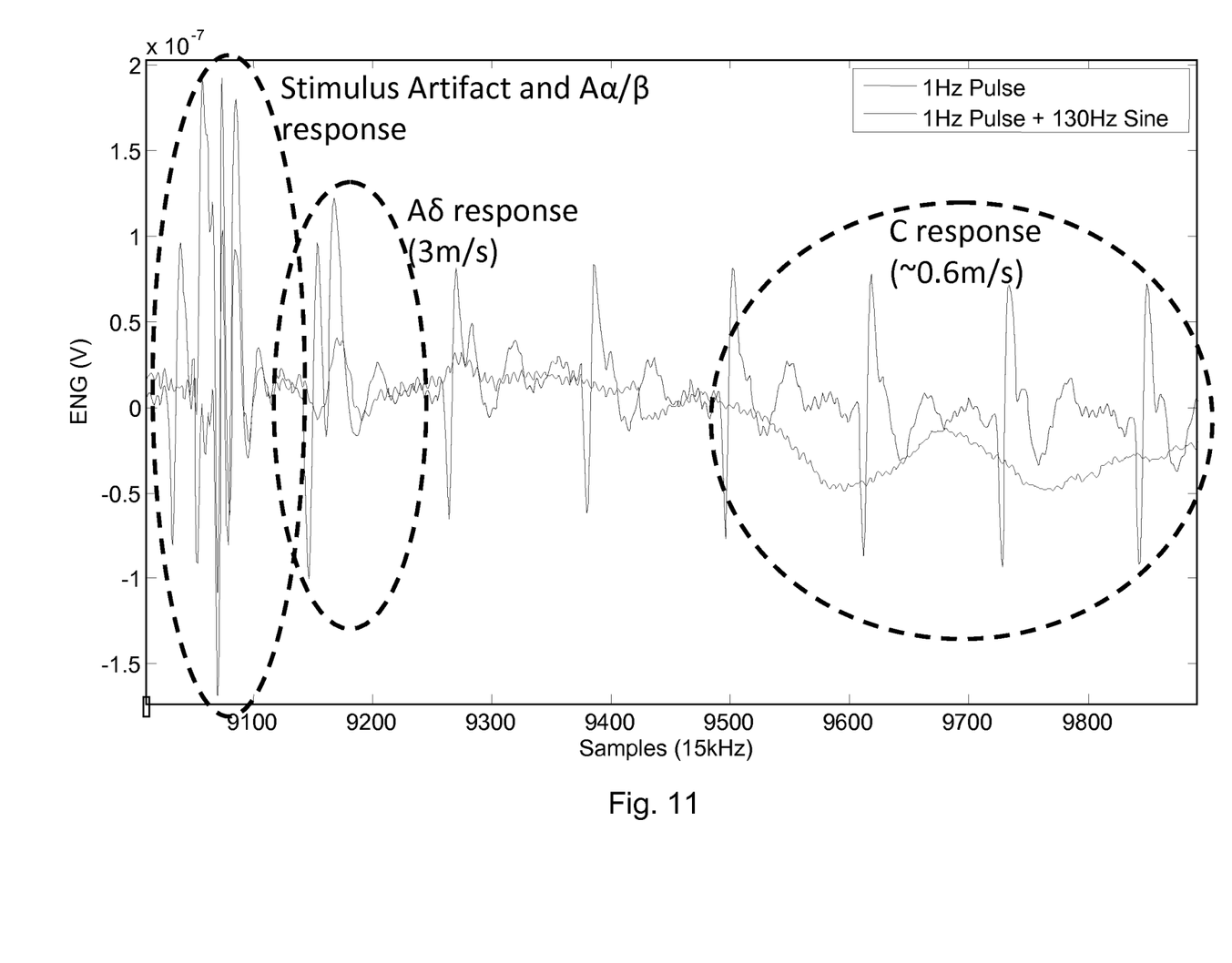
FIG. 11 is a plot of EMG twitch response versus a time scale illustrating the signal-transmission behavior of pain signals versus motor-neuron signals through the sural nerve based on electrical-current stimuli.

The solid line in the graph of FIG. 11 represents the EMG twitch response based on the 1 Hz pulse alone, and the broken line represents the EMG twitch response based on the two combined currents. To produce the data recorded in the broken line, the sinus signal has been filtered out. As can be seen from the solid (1 Hz pulse alone) line, the 1 Hz pulse induced a substantial EMG response very close to the time when the current was initially applied, which returned to baseline quickly and remained so until approximately 9500 on the time scale, when a second EMG response was recorded. Because large motor fibers are myelinated fibers, they exhibit very rapid signal transmission resulting in a very fast (and high frequency) response following the current application. Thus, the large-magnitude EMG response at the beginning of the time scale for the solid line represents motor-fiber recruitment via motor-signal transmission through myelinated fibers. Conversely, C-fibers are unmyelinated, and exhibit correspondingly much slower signal-transmission rates. The delayed EMG response that begins at approximately 9500 on the time scale for the solid line represents C-fiber transmission of pain signals. The response for these signals is delayed (and lower frequency) because they travel much more slowly than the motor signals through myelinated fibers. Now turning to the broken line, as with the solid line there is a large magnitude motor signal near time zero on the time scale, produced from the 1 Hz pulse. But there is no time-delayed C-fiber transmission signal. There are also periodic sharp motor signals of lesser magnitude resulting from the 130 Hz sine wave. But there is no corresponding C-fiber response. Instead, the 130 Hz sine wave has suppressed the C-fiber pain response that would otherwise have resulted from the 1 Hz pulse responsible for the initial, high-magnitude motor response. In this case, the 130 Hz sinusoid produced repetitive motor unit stimulation because a longitudinal rather than transverse field was used.

The following references are noted in connection with the present disclosure. Each of these references is incorporated herein by reference in their entirety.

[1] Bouhassira D, Lanteri-Minet M, Attal N, Laurent B, Touboul C (June 2008). "Prevalence of chroniC pain with neuropathic characteristics in the general population," *Pain* 136 (3): 380-7.

[2] Torrance N, Smith B H, Bennett M I, Lee A J (April 2006). "The epidemiology of chronic pain of predominantly neuropathic origin. Results from a general population survey." *J Pain* 7 (4): 281-9

[3] A E Yakovlev, and Y Elllas. "Spinal Cord Stimulation as a Treatment Option for Intractable Neuropathic Cancer Pain" *Clinical Medicine & Research Volume* 6, Number 3-4: 103-106.

[4] Z. Lertmanorat and D. M. Durand: Electrode array for reversing the recruitment order of peripheral nerve stimulation: Experimental studies, Annals of Biomedical Engineering, January; 34(1):152-60, 2006

Although the invention has been described with respect to certain preferred embodiments, it is to be understood that the invention is not limited by the embodiments herein disclosed, which are exemplary and not limiting in nature, but is to include all modifications and adaptations thereto as would occur to the person having ordinary skill in the art upon reviewing the present disclosure, and as fall within the spirit and the scope of the invention as set forth in the appended claims.

What is claimed is:

1. A method for treatment of pain, comprising:
   generating, by a power supply device, a non-pulsed electrical current comprising a frequency between 10 Hz and 2000 Hz and a rise time from 0 to a peak amplitude of at least 10 μs;
   supplying the non-pulsed electrical current to at least two electrodes at diametrically opposed locations about the peripheral nerve;
   applying, by the at least two electrodes, the non-pulsed electrical current through the peripheral nerve in a direction substantially transverse to a longitudinal axis of the peripheral nerve; and
   inhibiting conduction of C-fibers in the peripheral nerve based on the application of the non-pulsed electrical current to prevent the transmission of pain signals, wherein motor nerve fibers and higher-sensory nerve fibers in the peripheral nerve are not substantially activated based on the application of the non-pulsed electrical current.

2. The method of claim 1, wherein the frequency is between 10 Hz and 500 Hz.

3. The method of claim 1, wherein the frequency is between 10 Hz and 150 Hz.

4. The method of claim 1, wherein the frequency is about 130 Hz.

5. The method of claim 1, wherein the non-pulsed electrical current comprises a charge-balanced waveform.

6. The method of claim 1, wherein the non-pulsed electrical current comprises an analog waveform that exhibits a rise time between neutral and peak amplitude of at least 10 μs.

7. The method of claim 6, wherein the rise time is at least 20 μs.

8. The method of claim 6, wherein the analog waveform comprises a sinusoid.

9. The method of claim 6, wherein the analog waveform comprises a declining segment that exhibits an instantaneous step from peak amplitude to neutral.

10. The method of claim 1, wherein the non-pulsed electrical current comprises a digital waveform comprising a series of discrete steps whose sum approximates an analog waveform having a rise time between neutral and peak amplitude of at least 10 μs.

11. The method of claim 10, wherein the frequency is between 10 and 20 Hz or at least 40 Hz.

12. The method of claim 10, wherein the rise time is at least 1000 μs.

13. The method of claim 10, wherein the digital waveform approximates a sinusoid.

14. The method of claim 1, wherein the non-pulsed electrical current comprises an amplitude between 0.4 mA and 5 mA.

15. The method of claim 1, further comprising simultaneously applying a second current, independent from the non-pulsed electrical current, through the peripheral nerve to inhibit or suppress transmission of motor signals through motor fibers in the peripheral nerve.

16. The method of claim 1, wherein the non-pulsed electrical current consisting of one or more non-pulsed electrical waveforms.

17. The method of claim 1, wherein the non-pulsed electrical current comprises a triangular waveform.

18. The method of claim 1, wherein the non-pulsed electrical current comprises a trapezoidal waveform.

19. The method of claim 1, wherein the non-pulsed electrical current comprises at least one of a logarithmic waveform and an exponential waveform.

* * * * *